United States Patent [19]
Hannah et al.

[11] Patent Number: 5,589,618
[45] Date of Patent: Dec. 31, 1996

[54] MATERIALS AND METHODS FOR INCREASING CORN SEED WEIGHT

[75] Inventors: L. Curtis Hannah, Gainesville, Fla.; Michael Giroux, Pullman, Wash.

[73] Assignee: University of Florida, Gainesville, Fla.

[21] Appl. No.: 299,675

[22] Filed: Sep. 1, 1994

[51] Int. Cl.$^6$ ............................. A01H 4/00; C12N 15/05
[52] U.S. Cl. .................. 800/205; 800/250; 800/DIG. 56; 536/23.1; 536/23.2; 536/23.6; 435/172.3; 935/9; 935/10
[58] Field of Search .......................... 800/205; 536/23.1, 536/23.2, 23.6; 935/9, 10; 435/172.3

[56] References Cited

PUBLICATIONS

Steel et al. (1960) Principles and Procedures of Statistics. Mcgraw–Hill Book Company, Inc. New York. pp. 400–403.
Giroux et al. (1994) De novo synthesis of an intron by the maize transposable element Dissociation. PNAS vol. 91. pp. 12150–12154. Dec.
Bae, J. M., M. Giroux, L. Hannah (1990) "Cloning and Characterization of the Brittle–2 Gene of Maize" Maydica 35:317–322.
Anderson, J. M. et al. (1989) "The Encoded Primary Sequence of a Rice Seed ADP–glucose Pyrophosphorylase Subunit and Its Homology to the Bacterial Enzyme" The Journal of Biological Chemistry 264(21):12238–12242.
Anderson, J. M. et al. (1991) "Molecular characterization of the gene encoding a rice endosperm–specific ADPglucose pyrophosphorylase subunit and its developmental pattern of transcription" Gene 97:199–205.
Copeland, Les, Jack Preiss (1981) "Purification of Spinach Leaf ADPglucose Pyrophosphorylase" Plant Physiol. 68:996–1001.
Dickinson, David B., Jack Preiss (1969) "Presence of ADP–glucose Pyrophosphorylase in Shrunken–2 and Brittle–2 Mutants of Maize Endosperm" Plant Physiol. 44:1058–1062.
Hannah, L. Curtis, Oliver E. Nelson, Jr. (1975) "Characterization of Adenosine Diphosphate Glucose Puyrophosphorylases from Developing Maize Seeds" Plant Physiol. 55:297–302.
Hannah, L. C., O. E. Nelson, Jr. (1976) "Characterization of ASP–Glucose Pyrophosphorylase from Shrunken–2 and Brittle–2 Mutants of Maize" Biochemical Genetics 14(7/8):547–560.

Lin, Tsan–Piao et al. (1988) "A Starch Deficient Mutant of Arabidopsis thaliana with Low ADPglucose Pyrophosphorylase Activity Lacks One of the Two Subunits of the Enzyme" Plant Physiol. 88:1175–1181.
Nakata, Paul A. et al. (1991) "Comparison of the primary sequences of two potato tuber ADP–glucose pyrophosphorylase subunits" Plant Molecular Biology 17:1089–1093.
Okita, Thomas W. et al. (1990) "The Subunit Structure of Potato Tuber ADPglucose Pyrophosphorylase" Plant Physiol. 93:785–790.
Olive, Mark R. et al. (1989) "Isolation and nucleotide sequences of cDNA clones encosing ADP–glucose pyrophosphorylase polypeptides from wheat leaf and endosperm" Plant Molecular Biology 12:525–538.
Preiss, J. (1984) "Bacterial Glycogen Synthesis and Its Regulation" Ann. Rev. Microbiol. 38:419–458.
Tsai, Chia–Yin, Oliver E. Nelson (1966) "Starch–Deficient Maize Mutant Lacking Adenosine Diphosphate Glucose Pyrophosphorylases Activity" Science 151:341–343.
Shaw, Janine R., L. Curtis Hannah (1992) "Genomic Nucleotide Sequence of a Wild–Type Shrunken–2 Allele of Zea mays" Plant Physiol. 98:1214–1216.
Bhave, M. R. et al. (1990) "Identification and Molecular Characterization of Shrunken–2 cDNA Clones of Maize" The Plant Cell 2:581–588.
Muller–Rober, B. T. et al. (1990) "One of two different ADP–glucose pyrophosporylase genes from potato responds strongly to elevated levels of sucrose" Mol. Gen. Genet. 224:136–146.
Morell, M., M. Bloom, J. Preiss (1988) "Affinity Labeling of the Allosteric Activator Site(s) of Spinich Leaf ADP–glucose Pyrophosphorylase" The Journal of Biological Chemistry 263(2):633–637.
Stark, D. M. et al. (1992) "Regulation of the Amount of Starch in Plant Tissues by ADP Glucose Pyrophosphorylase" Science 258:287–292.

Primary Examiner—Gary Benzion
Attorney, Agent, or Firm—Saliwanchik & Saliwanchik

[57] ABSTRACT

The subject invention pertains to a novel variant of the maize gene, Shrunken2 (Sh2) and a method of using that gene. The variant gene, Sh2-m1Rev6, encodes a subunit of the ADP-glucose pyrophosphorylase (AGP) enzyme that has additional amino acids inserted near or in the allosteric binding site of the protein. Corn seed expressing the Sh2-m1Rev6 gene has a 15% weight increase over wild type seed. The increase in seed weight is not associated simply with an increase in percentage starch content of the seed.

10 Claims, No Drawings

MATERIALS AND METHODS FOR INCREASING CORN SEED WEIGHT

This invention was made with government support under National Science Foundation grant number 93052818. The government has certain rights in this invention.

BACKGROUND OF THE INVENTION

ADP-glucose pyrophosphorylase (AGP) catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (*Zea mays*) endosperm (Tsai and Nelson, 1966; Dickinson and Preiss, 1969).

AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland and Preiss, 1981; Morell et al., 1987). Immunological analysis using antiserum prepared against the small and large subunits of spinach leaf showed that potato tuber AGP is also encoded by two genes (Okita et al., 1990). The cDNA clones of the two subunits of potato tuber (50 and 51 kDa) have also been isolated and sequenced (Muller-Rober et al., 1990; Nakata et al., 1991).

As Hannah and Nelson (Hannah and Nelson, 1975 and 1976) postulated, both Shrunken-2 (Sh2) (Bhave et al., 1990) and Brittle-2 (Bt2) (Bae et al., 1990) are structural genes of maize endosperm ADP-glucose pyrophosphorylase. Sh2 and Bt2 encode the large subunit and small subunit of the enzyme, respectively. From cDNA sequencing, Sh2 and Bt2 proteins have predicted molecular weight of 57,179 Da (Shaw and Hannah, 1992) and 52,224 Da, respectively. The endosperm is the site of most starch deposition during kernel development in maize. Sh2 and bt2 maize endosperm mutants have greatly reduced starch levels corresponding to deficient levels of AGP activity. Mutations of either gene have been shown to reduce AGP activity by about 95% (Tsai and Nelson, 1966; Dickinson and Preiss, 1969). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. placed a mutant form of *E. coli* AGP in potato tuber and obtained a 35% increase in starch content (Stark, 1992).

The cloning and characterization of the genes encoding the AGP enzyme subunits have been reported for various plants. These include Sh2 cDNA (Bhave et al., 1990), Sh2 genomic DNA (Shaw and Hannah, 1992), and Bt2 cDNA (Bae et al., 1990) from maize; small subunit cDNA (Anderson et al., 1989) and genomic DNA (Anderson et al., 1991) from rice; and small and large subunit cDNAs from spinach leaf (Morell et al., 1987) and potato tuber (Muller-Rober et al., 1990; Nakata et al., 1991). In addition, cDNA clones have been isolated from wheat endosperm and leaf tissue (Olive et al., 1989) and *Arabidopsis thaliana* leaf (Lin et al., 1988).

AGP functions as an allosteric enzyme in all tissues and organisms investigated to date. The allosteric properties of AGP were first shown to be important in *E. coli*. A glycogen-overproducing *E. coli* mutant was isolated and the mutation mapped to the structural gene for AGP, designated as glyC. The mutant *E. coli*, known as glyC-16, was shown to be more sensitive to the activator, fructose 1,6 bisphosphate, and less sensitive to the inhibitor, cAMP (Preiss, 1984). Although plant AGP's are also allosteric, they respond to different effector molecules than bacterial AGP's. In plants, 3-phosphoglyceric acid (3-PGA) functions as an activator while phosphate ($PO_4$) serves as an inhibitor (Dinkinson and Preiss, 1969).

In view of the fact that endosperm starch content comprises approximately 70% of the dry weight of the seed, alterations in starch biosynthesis correlate with seed weight. Unfortunately, the undesirable effect associated with such alterations has been an increase in the relative starch content of the seed. Therefore, the development of a method for increasing seed weight in plants without increasing the relative starch content of the seed is an object of the subject invention.

BRIEF SUMMARY OF THE INVENTION

The subject invention concerns a novel variant of the Shrunken-2 (Sh2) gene from maize. The Sh2 gene encodes ADP-glucose pyrophosphorylase (AGP), an important enzyme involved in starch synthesis in the major part of the corn seed, the endosperm. In a preferred embodiment, the novel gene of the subject invention encodes a variant AGP protein which has two additional amino acids inserted into the sequence. The variant gene described herein has been termed the Sh2-m1Rev6 gene. Surprisingly, the presence of the Sh2-m1Rev6 gene in a corn plant results in a substantial increase in corn seed weight when compared to wild type seed weight, but does so in the absence of an increase in the relative starch content of the kernel.

The subject invention further concerns a method of using the variant sh2 gene in maize to increase seed weight. The subject invention also concerns plants having the variant sh2 gene and expressing the mutant protein in the seed endosperm.

As described herein, the sh2 variant, Sh2-m1Rev6, can be produced using in vivo, site-specific mutagenesis. A transposable element was used to create a series of mutations in the sequence of the gene that encodes the enzyme. As a result, the Sh2-m1Rev6 gene encodes an additional amino acid pair within the allosteric binding site of the protein.

BRIEF DESCRIPTION OF THE SEQUENCES

SEQ ID NO. 1 is the genomic nucleotide sequence of the Sh2-m1Rev6 gene.

SEQ ID NO. 2 is the amino acid sequence of the protein encoded by the Sh2-m1Rev6 gene.

DETAILED DISCLOSURE OF THE INVENTION

The subject invention provides a novel variant of the Shrunken-2 (Sh2) gene and a method for increasing seed weight in a plant through the expression of the variant sh2 gene. The Sh2 gene encodes a subunit of the enzyme ADP-glucose pyrophosphorylase (AGP) in maize endosperm. The variant gene, denoted herein as Sh2- m1Rev6, contains a mutation that encodes an additional arginine:threonine amino acid pair compared to the wild type protein. The sequences of the wild type DNA and protein are disclosed in Shaw and Hannah, 1992. The in vivo, site-specific mutation which resulted in the arginine:threonine insertion was generated in Sh2 using the transposable element, dissociation (Ds), which can insert into, and be excised from, the Sh2 gene under appropriate conditions. Ds excision can alter gene expression through the addition of nucleotides to a gene at the site of excision of the element.

In a preferred embodiment, insertion mutations in the Sh2 gene were obtained by screening for germinal revertants after excision of the Ds transposon from the gene. The revertants were generated by self-pollination of a stock containing the Ds-Sh2 mutant allele, the Activator (Ac) element of this transposable element system, and appropriate outside markers. The Ds element can transpose when the Ac element is present. Wild type seed were selected, planted, self-pollinated and crossed onto a tester stock. Results from this test cross were used to remove wild type alleles due to pollen contamination. Seeds homozygous for each revertant allele were obtained from the self-progeny. Forty-four germinal revertants of the Ds-induced sh2 mutant were collected.

Cloning and sequencing of the Ds insertion site showed that the nucleotide insertion resides in the area of the gene that encodes the binding site for the AGP activator, 3-PGA (Morrell, 1988). Of the 44 germinal revertants obtained, 28 were sequenced. The sequenced revertants defined 5 isoalleles of sh2: 13 restored the wild type sequence, 11 resulted in the insertion of the amino acid tyrosine, two contained an additional proline, one revertant contained a two amino acid insertion, leucine:leucine, and the last one, designated as Sh2-m1Rev6, contained the two amino acid insertion, arginine:threonine. The Sh2-m1Rev6 variant encodes an AGP enzyme subunit that has the arginine:threonine amino acid pair inserted between the tyrosine and isoleucine at amino acid residues 503 and 504, respectively, of the native protein.

Surprisingly, the expression of the Sh2-m1Rev6 gene in maize resulted in a significant increase in seed weight over that obtained from maize expressing the wild-type Sh2 allele. Moreover, seeds from plants having the Sh2-m1Rev6 gene contained approximately the same percentage starch content relative to any of the other revertants generated. In a preferred embodiment, the Sh2-m1Rev6 gene is contained in homozygous form within the genome of a plant seed.

The subject invention further concerns a plant that has the Sh2-m1Rev6 gene incorporated into its genome. In a preferred embodiment, the plant is a monocotyledonous species. More preferably, the plant may be *Zea mays*. Plants having the Sh2-m1Rev6 gene can be grown from seeds that have the gene in their genome. In addition, techniques for transforming plants with a gene are known in the art.

Because of the degeneracy of the genetic code, a variety of different polynucleotide sequences can encode the variant AGP polypeptide disclosed herein. In addition, it is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by Sh2-m1Rev6. The subject invention also contemplates those polynucleotide molecules having sequences which are sufficiently homologous with the wild type Sh2 DNA sequence so as to permit hybridization with that sequence under standard high-stringency conditions. Such hybridization conditions are conventional in the art (see, e.g., Maniatis et al., 1989).

The polynucleotide molecules of the subject invention can be used to transform plants to express the Sh2-m1Rev6 allele in those plants. In addition, the polynucleotides of the subject invention can be used to express the recombinant variant AGP enzyme. They can also be used as a probe to detect related enzymes. The polynucleotides can also be used as DNA sizing standards.

The polypeptides encoded by the polynucleotides of the subject invention can be used to catalyze the conversion of ATP and α-glucose-1-phosphate to ADP-glucose and pyrophosphate, or to raise an immunogenic response to the AGP enzymes and variants thereof. They can also be used as molecular weight standards, or as an inert protein in an assay.

The following are examples which illustrate procedures and processes, including the best mode, for practicing the invention. These examples should not be construed as limiting, and are not intended to be a delineation of all possible modifications to the technique. All percentages are by weight and all solvent mixture proportions are by volume unless otherwise noted.

Example 1—Expression of Sh2-m1Rev6 Gene in Maize Endosperm

Homozygous plants of each revertant obtained after excision of the Ds transposon were crossed onto the F1 hybrid corn, "Florida Stay Sweet." This sweet corn contains a null allele for the Sh2 gene, termed sh2-R. Resulting endosperms contained one dose of the functional allele from a revertant and two female-derived null alleles, denoted by the following genotype Sh2-m1RevX/sh2-R/sh2-R, where X represents one of the various isoalleles of the revertants. Crosses were made during two growing seasons.

Resulting seed weight data for each revertant and wild type seed are shown in Table 1. The first column shows the amino acid insertion in the AGP enzyme obtained after the in vivo, site-specific mutagenesis.

TABLE 1

| Sequence alteration | # of revertants | Average Seed weight | Standard deviation |
|---|---|---|---|
| wild type | 13 | 0.250 grams | 0.015 |
| tyrosine | 11 | 0.238 grams | 0.025 |
| proline | 2 | 0.261 grams | 0.014 |
| leu,leu | 1 | 0.223 grams | nd* |
| arg,thr (Rev6) | 1 | 0.289 grams | 0.022 |

*nd = not determined

The data shown in Table 1 represents the average kernel seed weight for each revertant over the course of two growing seasons. The expression of the Sh2-m1Rev6 gene to produce the Rev6 mutant AGP subunit gave rise to an almost 16% increase in seed weight in comparison to the wild type revertant.

In addition, starch content was determined on the kernels analyzed above using various methodologies. The analysis showed that Sh2-m1Rev6 containing kernels were no higher in percentage starch relative to kernels expressing the other alleles shown in the table above. Therefore, it appears that the increase in seed weight is not solely a function of starch content.

Corn seeds that contain at least one functional Sh2-m1Rev6 allele have been deposited with the American Type Culture Collection (ATCC), 12301 Parklawn Drive, Rockville, Md. 20852 U.S.A., on May 16, 1996 and assigned accession number ATCC 97624. The culture will be assigned an accession number by the repository.

The seeds have been deposited under conditions that assure that access to the culture will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject seed deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject seed deposit will be irrevocably removed upon the granting of a patent disclosing it.

As would be apparent to a person of ordinary skill in the art, seeds and plants that are homozygous for the Sh2-m1Rev6 allele can be readily prepared from heterozygous seeds using techniques that are standard in the art. In addition, the Sh2-m1Rev6 gene can be readily obtained from the deposited seeds.

It should be understood that the examples and embodiments described herein are for illustrative purposes only and that various modifications or changes in light thereof will be suggested to persons skilled in the art and are to be included within the scope and purview of this application and the scope of the appended claims.

REFERENCES

Anderson, J. M., J. Hnilo, R. Larson, t. W. Okita, M. Morell, J. Preiss (1989), "The encoded primary sequence of a rice seed ADP-glucose pyrophosphorylase subunit and its homology to the bacterial enzyme," *J. Biol. Chem.* 264:12238–12242.

Anderson, J. M., R. Larson, D. Landencia, W. T. Kim, D. Morrow, T. W. Okita, J. Preiss (1991) "Molecular characterization of the gene encoding a rice endosperm-specific ADP-glucose pyrophosphorylase subunit and its developmental pattern of transcription," *Gene* 97:199–205.

Bae, J. M., M. Giroux, L. C. Hannah (1990) "Cloning and characterization of the Brittle-2 gene of maize," *Maydica* 35:317–322.

Bhave, M. R., S. Lawrence, C. Barton, L. C. Hannah (1990) "Identification and molecular characterization of Shrunken-2 cDNA clones of maize," *Plant Cell* 2:581–588.

Copeland, L., J. Preiss (1981) "Purification of spinach leaf ADP-glucose pyrophosphorylase," *Plant Physiol.* 68:996–1001.

Dickinson, D. B., J. Preiss (1969) "Presence of ADP-glucose pyrophosphorylase in Shrunken-2 and Brittle-2 mutants of maize endosperm," *Plant Physiol.* 44:1058–1062.

Hannah, L. C., O. E. Nelson (1975) "Characterization of adenosine diphosphate glucose pyrophosphorylase from developing maize seeds," *Plant Physiol.* 55:297–302.

Hannah, L. C., O. E. Nelson (1976) "Characterization of adenosine diphosphate glucose pyrophosphorylase from Shrunken-2 and Brittle-2 mutants of maize," *Biochem. Genet.* 14:547–560.

Lin, T., T. Caspar, C. Somerville, J. Preiss (1988) "A starch deficient mutant of *Arabidopsis thaliana* with low ADP-glucose pyrophosphorylase activity lacks one of the two subunits of the enzyme," *Plant Physiol.* 88:1175–1181.

Maniatis, T., E. F. Fritsch, J. Sambrook (1989) *Molecular Cloning: A Laboratory Manual,* 2d Edition, Cold Spring Harbor Laboratory, Cold Spring Harbor, N.Y.

Morell, M., M. Bloon, V. Knowles, J. Preiss (1988) "Subunit structure of spinach leaf ADP-glucose pyrophosphorylase," *J. Bio. Chem.* 263:633.

Muller-Rober, B. T., J. Kossmann, L. C. Hannah, L. Willmitzer, U. Sounewald (1990) "One of the two different ADP-glucose pyrophosphorylase genes from potato responds strongly to elevated levels of sucrose," *Mol. Gen. Genet.* 224:136–146.

Nakata, P. A., T. W. Greene, J. M. Anderson, B. J. Smith-White, T. W. Okita; J. Preiss (1991) "Comparison of primary sequences of two potato tuber ADP-glucose pyrophosphorylase subunits," *Plant Mol. Biol.* 17:1089–1093.

Okita, T. W., P. A. Nakata, J. M. Anderson, J. Sowokinos, M. Morell, J. Preiss (1990) "The subunit structure of potato tuber ADP-glucose pyrophosphorylase," *Plant Physiol.* 93:785–790.

Olive, M. R., R. J. Ellis, W. W. Schuch (1989) "Isolation and nucleotide sequences of cDNA clones encoding ADP-glucose pyrophosphorylase polypeptides from wheat leaf and endoosperm," *Plant Physiol. Mol. Biol.* 12:525–538.

Preiss, J. (1984) "Bacterial glycogen synthesis and it regulation," *Ann. Rev. Microbiol.* 38:105.

Shaw, J. R., L. C. Hannah (1992) "Genomic nucleotide sequence of a wild type Shrunken-2 allele of *Zea mays,*" *Plant Physiol.* 98:1214–1216.

Starke, et al. (1992) "Regulation of the amount of starch in plant tissues by ADP-glucose pyrophosphorylase," *Science* 258:287.

Tsai, C., O. E. Nelson (1966) "Starch-deficient maize mutant lacking adenosine diphosphate glucose pyrophosphorylase activity," *Science* 151:341–343.

We claim:

1. A polynucleotide molecule, comprising a variant of the wild type shrunken-2 (Sh2) gene, wherein said variant codes for the insertion of at least one additional amino acid within the allosteric binding site of the ADP-glucose pyrophosphorylase (AGP) enzyme subunit, whereby a plant expressing said polynucleotide molecule has increased seed weight relative to the seed weight of a plant expressing the wild type Sh2 gene.

2. The polynucleotide molecule, according to claim 1, wherein said polynucleotide molecule encodes the amino acid pair arginine:threonine, wherein said amino acid pair is inserted between amino acids 503 and 504 of the native AGP enzyme subunit.

3. The polynucleotide molecule, according to claim 1, wherein the AGP enzyme encoded by said polynucleotide molecule consists essentially of the amino acid sequence shown in SEQ ID NO. 2.

4. The polynucleotide molecule, according to claim 3, wherein the nucleotide sequence encoding SEQ ID NO.2 consists of the sequence shown in SEQ ID NO.1 or a degenerate fragment thereof, wherein a plant expressing said polynucleotide molecule has increased seed weight relative to the seed weight of a plant expressing the wild type Sh2 gene.

5. A method for increasing the seed weight of a plant, comprising incorporating the polynucleotide molecule of claim 1 into the genome of said plant and expressing said polynucleotide.

6. The method, according to claim 5, wherein said plant is *Zea mays*.

7. A plant seed comprising the polynucleotide molecule of claim 1 within the genome of said seed.

8. A plant expressing the polynucleotide molecule of claim 1.

9. The plant, according to claim 8, wherein said plant is *Zea mays*.

10. The plant, according to claim 8, wherein said plant is grown from the seed of claim 7.

* * * * *

UNITED STATES PATENT AND TRADEMARK OFFICE
CERTIFICATE OF CORRECTION

PATENT NO. : 5,589,618
DATED : December 31, 1996
INVENTOR(S) : L. Curtis Hannah, et al.

It is certified that error appears in the above-identified patent and that said Letters Patent is hereby corrected as shown below:

Column 2, line 58: "encoded:by" should read --encoded by--.

Column 3, line 28: "encodes-the" should read --encodes the --;

line 60: "in the an" should read --in the art--.

Column 6, line 40: "Okita; J." should read --Okita, J.--.

Signed and Sealed this

Second Day of December, 1997

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 7745 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| TAAGAGGGGT | GCACCTAGCA | TAGATTTTTT | GGGCTCCCTG | GCCTCTCCTT | TCTTCCGCCT | 60 |
| GAAAACAACC | TACATGGATA | CATCTGCAAC | CAGAGGGAGT | ATCTGATGCT | TTTTCCTGGG | 120 |
| CAGGGAGAGC | TATGAGACGT | ATGTCCTCAA | AGCCACTTTG | CATTGTGTGA | AACCAATATC | 180 |
| GATCTTTGTT | ACTTCATCAT | GCATGAACAT | TTGTGGAAAC | TACTAGCTTA | CAAGCATTAG | 240 |
| TGACAGCTCA | GAAAAAAGTT | ATCTCTGAAA | GGTTTCATGT | GTACCGTGGG | AAATGAGAAA | 300 |
| TGTTGCCAAC | TCAAACACCT | TCAATATGTT | GTTTGCAGGC | AAACTCTTCT | GGAAGAAAGG | 360 |
| TGTCTAAAAC | TATGAACGGG | TTACAGAAAG | GTATAAACCA | CGGCTGTGCA | TTTTGGAAGT | 420 |
| ATCATCTATA | GATGTCTGTT | GAGGGGAAAG | CCGTACGCCA | ACGTTATTTA | CTCAGAAACA | 480 |
| GCTTCAACAC | ACAGTTGTCT | GCTTTATGAT | GGCATCTCCA | CCCAGGCACC | CACCATCACC | 540 |
| TATTCACCTA | TCTCTCGTGC | CTGTTTATTT | TCTTGCCCTT | TCTGATCATA | AAAAATCATT | 600 |
| AAGAGTTTGC | AAACATGCAT | AGGCATATCA | ATATGCTCAT | TTATTAATTT | GCTAGCAGAT | 660 |
| CATCTTCCTA | CTCTTTACTT | TATTTATTGT | TTGAAAAATA | TGTCCTGCAC | CTAGGGAGCT | 720 |
| CGTATACAGT | ACCAATGCAT | CTTCATTAAA | TGTGAATTTC | AGAAAGGAAG | TAGGAACCTA | 780 |
| TGAGAGTATT | TTTCAAAATT | AATTAGCGGC | TTCTATTATG | TTTATAGCAA | AGGCCAAGGG | 840 |
| CAAAATCGGA | ACACTAATGA | TGGTTGGTTG | CATGAGTCTG | TCGATTACTT | GCAAGAAATG | 900 |
| TGAACCTTTG | TTTCTGTGCG | TGGGCATAAA | ACAAACAGCT | TCTAGCCTCT | TTACGGTAC | 960 |
| TTGCACTTGC | AAGAAATGTG | AACTCCTTTT | CATTTCTGTA | TGTGGACATA | ATGCCAAAGC | 1020 |
| ATCCAGGCTT | TTTCATGGTT | GTTGATGTCT | TTACACAGTT | CATCTCCACC | AGTATGCCCT | 1080 |
| CCTCATACTC | TATATAAACA | CATCAACAGC | ATCGCAATTA | GCCACAAGAT | CACTTCGGGA | 1140 |
| GGCAAGTGTG | ATTTCGACCT | TGCAGCCACC | TTTTTTTGTT | CTGTTGTAAG | TATACTTTCC | 1200 |
| CTTACCATCT | TTATCTGTTA | GTTTAATTTG | TAATTGGGAA | GTATTAGTGG | AAAGAGGATG | 1260 |
| AGATGCTATC | ATCTATGTAC | TCTGCAAATG | CATCTGACGT | TATATGGGCT | GCTTCATATA | 1320 |
| ATTTGAATTG | CTCCATTCTT | GCCGACAATA | TATTGCAAGG | TATATGCCTA | GTTCCATCAA | 1380 |
| AAGTTCTGTT | TTTTCATTCT | AAAAGCATTT | TAGTGGCACG | CAATTTTGTC | CATGAGGGAA | 1440 |
| AGGAAATCTG | TTTTGGTTAC | TTTGCTTGAG | GTGCATTCTT | CATATGTCCA | GTTTTATGGA | 1500 |
| AGTAATAAAC | TTCAGTTTGG | TCATAAGATG | TCATATTAAA | GGGCAAACAT | ATATTCAATG | 1560 |
| TTCAATTCAT | CGTAAATGTT | CCCTTTTTGT | AAAAGATTGC | ATACTCATTT | ATTTGAGTTG | 1620 |
| CAGGTGTATC | TAGTAGTTGG | AGGAGATATG | CAGTTTGCAC | TTGCATTGGA | CACGAACTCA | 1680 |
| GGTCCTCACC | AGATAAGATC | TTGTGAGGGT | GATGGGATTG | ACAGGTTGGA | AAAATTAAGT | 1740 |
| ATTGGGGGCA | GAAAGCAGGA | GAAAGCTTTG | AGAAATAGGT | GCTTGGTGG | TAGAGTTGCT | 1800 |

| | | | | | | |
|---|---|---|---|---|---|---|
| GCAACTACAC | AATGTATTCT | TACCTCAGAT | GCTTGTCCTG | AAACTCTTGT | AAGTATCCAC | 1860 |
| CTCAATTATT | ACTCTTACAT | GTTGGTTTAC | TTTACGTTTG | TCTTTTCAAG | GGAAATTTAC | 1920 |
| TGTATTTTTT | GTGTTTTGTG | GGAGTTCTAT | ACTTCTGTTG | GACTGGTTAT | TGTAAAGATT | 1980 |
| TGTTCAAATA | GGGTCATCTA | ATAATTGTTT | GAAATCTGGG | AACTGTGGTT | TCACTGCGTT | 2040 |
| CAGGAAAAAG | TGAATTATTG | GTTACTGCAT | GAATAACTTA | TGGAAATAGA | CCTTAGAGTT | 2100 |
| GCTGCATGAT | TATCACAAAT | CATTGCTACG | ATATCTTATA | ATAGTTCTTT | CGACCTCGCA | 2160 |
| TTACATATAT | AACTGCAACT | CCTAGTTGCG | TTCAAAAAAA | AAAATGCAAC | TCTTAGAACG | 2220 |
| CTCACCAGTG | TAATCTTTCC | TGAATTGTTA | TTTAATGGCA | TGTATGCACT | ACTTGTATAC | 2280 |
| TTATCTAGGA | TTAAGTAATC | TAACTCTAGG | CCCCATATTT | GCAGCATTCT | CAAACACAGT | 2340 |
| CCTCTAGGAA | AAATTATGCT | GATGCAAACC | GTGTATCTGC | TATCATTTTG | GGCGGAGGCA | 2400 |
| CTGGATCTCA | GCTCTTTCCT | CTGACAAGCA | CAAGAGCTAC | GCCTGCTGTA | AGGGATAACA | 2460 |
| CTGAACATCC | AACGTTGATT | ACTCTATTAT | AGTATTATAC | AGACTGTACT | TTTCGAATTT | 2520 |
| ATCTTAGTTT | TCTACAATAT | TTAGTGGATT | CTTCTCATTT | TCAAGATACA | CAATTGATCC | 2580 |
| ATAATCGAAG | TGGTATGTAA | GACAGTGAGT | TAAAAGATTA | TATTTTTGG | GAGACTTCCA | 2640 |
| GTCAAATTTT | CTTAGAAGTT | TTTTGGTCC | AGATGTTCAT | AAAGTCGCCG | CTTTCATACT | 2700 |
| TTTTTAATT | TTTAATTGG | TGCACTATTA | GGTACCTGTT | GGAGGATGTT | ACAGGCTTAT | 2760 |
| TGATATCCCT | ATGAGTAACT | GCTTCAACAG | TGGTATAAAT | AAGATATTTG | TGATGAGTCA | 2820 |
| GTTCAATTCT | ACTTCGCTTA | ACCGCCATAT | TCATCGTACA | TACCTTGAAG | GCGGGATCAA | 2880 |
| CTTTGCTGAT | GGATCTGTAC | AGGTGATTTA | CCTCATCTTG | TTGATGTGTA | ATACTGTAAT | 2940 |
| TAGGAGTAGA | TTTGTGTGGA | GAGAATAATA | AACAGATGCC | GAGATTCTTT | TCTAAAAGTC | 3000 |
| TAGATCCAAA | GGCATTGTGG | TTCAAAACAC | TATGGACTTC | TACCATTTAT | GTCATTACTT | 3060 |
| TGCCTTAATG | TTCCATTGAA | TGGGGCAAAT | TATTGATTCT | ACAAGTGTTT | AATTAAAAAC | 3120 |
| TAATTGTTCA | TCCTGCAGGT | ATTAGCGGCT | ACACAAATGC | CTGAAGAGCC | AGCTGGATGG | 3180 |
| TTCCAGGGTA | CAGCAGACTC | TATCAGAAAA | TTTATCTGGG | TACTCGAGGT | AGTTGATATT | 3240 |
| TTCTCGTTTA | TGAATGTCCA | TTCACTCATT | CCTGTAGCAT | TGTTTCTTTG | TAATTTTGAG | 3300 |
| TTCTCCTGTA | TTTCTTTAGG | ATTATTACAG | TCACAAATCC | ATTGACAACA | TTGTAATCTT | 3360 |
| GAGTGGCGAT | CAGCTTTATC | GGATGAATTA | CATGGAACTT | GTGCAGGTAT | GGTGTTCTCT | 3420 |
| TGTTCCTCAT | GTTTCACGTA | ATGTCCTGAT | TTTGGATTAA | CCAACTACTT | TTGGCATGCA | 3480 |
| TTATTTCCAG | AAACATGTCG | AGGACGATGC | TGATATCACT | ATATCATGTG | CTCCTGTTGA | 3540 |
| TGAGAGGTAA | TCAGTTGTTT | ATATCATCCT | AATATGAATA | TGTCATCTTG | TTATCCAACA | 3600 |
| CAGGATGCAT | ATGGTCTAAT | CTGCTTTCCT | TTTTTTCCC | TTCGGAAGCC | GAGCTTCTAA | 3660 |
| AAATGGGCTA | GTGAAGATTG | ATCATACTGG | ACGTGTACTT | CAATTCTTTG | AAAACCAAA | 3720 |
| GGGTGCTGAT | TTGAATTCTA | TGGTTAGAAA | TTCCTTGTGT | AATCCAATTC | TTTTGTTTTC | 3780 |
| CTTTCTTTCT | TGAGATGAAC | CCCTCTTTTA | GTTATTCCA | TGGATAACCT | GTACTTGACT | 3840 |
| TATTCAGAAA | TGATTTTCTA | TTTTGCTGTA | GAATCTGACA | CTAAAGCTAA | TAGCACTGAT | 3900 |
| GTTGCAGAGA | GTTGAGACCA | ACTTCCTGAG | CTATGCTATA | GATGATGCAC | AGAAATATCC | 3960 |
| ATACCTTGCA | TCAATGGGCA | TTTATGTCTT | CAAGAAAGAT | GCACTTTAG | ACCTTCTCAA | 4020 |
| GTAATCACTT | TCCTGTGACT | TATTTCTATC | CAACTCCTAG | TTTACCTTCT | AACAGTGTCA | 4080 |
| ATTCTTAGGT | CAAAATATAC | TCAATTACAT | GACTTTGGAT | CTGAAATCCT | CCCAAGAGCT | 4140 |
| GTACTAGATC | ATAGTGTGCA | GGTAAGTCTG | ATCTGTCTGG | AGTATGTGTT | CTGTAAACTG | 4200 |

```
TAAATTCTTC ATGTCAAAAA GTTGTTTTTG TTTCCAGTTT CCACTACCAA TGCACGATTT    4260
ATGTATTTC  GCTTCCATGC ATCATACATA CTAACAATAC ATTTTACGTA TTGTGTTAGG    4320
CATGCATTTT TACGGGCTAT TGGGAGGATG TTGGAACAAT CAAATCATTC TTTGATGCAA    4380
ACTTGGCCCT CACTGAGCAG GTACTCTGTC ATGTATTCTG TACTGCATAT ATATTACCTG    4440
GAATTCAATG CATAGAATGT GTTAGACCAT CTTAGTTCCA TCCTGTTTTC TTCAATTAGC    4500
TTATCATTTA ATAGTTGTTG GCTAGAATTT AAACACAAAT TTACCTAATA TGTTTCTCTC    4560
TTCAGCCTTC CAAGTTTGAT TTTTACGATC CAAAAACACC TTTCTTCACT GCACCCCGAT    4620
GCTTGCCTCC GACGCAATTG GACAAGTGCA AGGTATATGT CTTACTGAGC ACAATTGTTA    4680
CCTGAGCAAG ATTTGTGTA  CTTGACTTGT TCTCCTCCAC AGATGAAATA TGCATTTATC    4740
TCAGATGGTT GCTTACTGAG AGAATGCAAC ATCGAGCATT CTGTGATTGG AGTCTGCTCA    4800
CGTGTCAGCT CTGGATGTGA ACTCAAGGTA CATACTCTGC CAATGTATCT ACTCTTGAGT    4860
ATACCATTTC AACACCAAGC ATCACCAAAT CACACAGAAC AATAGCAACA AAGCCTTTTA    4920
GTTCCAAGCA ATTTAGGGTA GCCTAGAGTT GAAATCTAAC AAAACAAAAG TCAAAGCTCT    4980
ATCACGTGGA TAGTTGTTTT CCATGCACTC TTATTTAAGC TAATTTTTTG GGTATACTAC    5040
ATCCATTTAA TTATTGTTTT ATTGCTTCTT CCCTTTGCCT TTCCCCCATT ACTATCGCGT    5100
CTTAAGATCA TACTACGCAC TAGTGTCTTT AGAGGTCTCT GGTGGACATG TTCAAACCAT    5160
CTCAATCGGT GTTGGACAAG TTTTTCTTGA ATTTGTGCTA CACCTAACCT ATCACGTATG    5220
TCATCGTTTC AAACTCGATC CTTCCTGTAT CATCATAAAT CCAATGCAAC ATACGCATTT    5280
ATGCAACATT TATCTGTTGA ACATGTCATC TTTTTGTAGG TTAACATTAT GCACCATACA    5340
ATGTAGCATG TCTAATCATC ATCCTATAAA ATTTACATTT TAGCTTATGT GGTATCCTCT    5400
TGCCACTTAG AACACCATAT GCTTGATGCC ATTTCATCCA CCCTGCTTTG ATTCTATGGC    5460
TAACATCTTC ATTAATATCC TCGCCTCTCT GTATCATTGG TCCTAAATAT GGAAATACAT    5520
TCTTTCTGGG CACTACTTGA CCTTCCAAAC TAACGTCTCC TTTGCTCCTT TCTTGTGTGT    5580
AGTAGTACCG AAGTCACATC TCATATATTC GGTTTTAGTT CTACTAAGTC CCGGGTTCGA    5640
TCCCCCTCAG GGGTGAATTT CGGGCTTGGT AAAAAAAATC CCCTCGCTGT GTCCCGCCCG    5700
CTCTCGGGGA TCGATATCCT GCGCGCCACC CTCCGGCTGG GCATTGCAGA GTGAGCAGTT    5760
GATCGGCTCG TTAGTGATGG GGAGCGGGGT TCAAGGGTTT TCTCGGCCGG GACCATGTTT    5820
CGGTCTCTTA ATATAATGCC GGGAGGGCAG TCTTTCCCTC CCCGGTCGAG TTTTAGTTCT    5880
ACCGAGTCTA AAACCTTTGG ACTCTAGAGT CCCCTGTCAC AACTCACAAC TCTAGTTTTC    5940
TATTTACTTC TACCTAGCGT TTATTAATGA TCACTATATC GTCTGTAAAA AGCATACACC    6000
AATGTAATCC CCTTGTATGT CCCTTGTAAT ATTATCCATC ACAAGAAAAA AGGTAAGGC    6060
TCAAAGTTGA CTTTTGATAT AGTCCTATTC TAATCGAGAA GTCATCTGTA TCTTCGTCTC    6120
TTGTTCGAAC ACTAGTCACA AAATTTTTTG TACATGTTCT TAATGAGTCC AACGTAATAT    6180
TCCTTGATAT TTTGTCATAA GCCCTCATCA AGTCAATGAA ATCACGTGT  AGGTCCTTCA    6240
TTTGTTCCTT ATACTGCTCC ATCACTTGTC TCATTAAGAA AATCTCTCTC ATAGTTAACC    6300
TTTTGGCATG AAACAAAATC ACACAGAAGT TGTTTCCTTT TTTAAGATC  CCACACAAAA    6360
GAGGTTTGAT CTAAGGAATC TGGATCCCTG ACAGGTTTAT CAAAATCCTT TGTGTTTTTC    6420
TTAAAACTGA ATATTCCTCC AGCTTCTAGT ATTGATGTAA TATTCAATCT GTTTAGCAAG    6480
TGAACACCTT GGTTCTTGTT GTTACTGTAC CCCCCCCCCC CCCCCCCCC  CGAGGCCCAG    6540
ATTACCACGA CATGAATACA AGAATATTGA ACCCAGATCT AGAGTTTGTT TGTACTGTTG    6600
```

-continued

```
AAAATCGGTG ACAATTCATT TTGTTATTGC GCTTTCTGAT AACGACAGGA CTCCGTGATG    6660
ATGGGAGCGG ACACCTATGA AACTGAAGAA GAAGCTTCAA AGCTACTGTT AGCTGGGAAG    6720
GTCCCAGTTG GAATAGGAAG GAACACAAAG ATAAGGTGAG TATGGATGTG GAACCACCGG    6780
TTAGTTCCCA AAAATATCAC TCACTGATAC CTGATGGTAT CCTCTGATTA TTTTCAGGAA    6840
CTGTATCATT GACATGAATG CTAGGATTGG GAAGAACGTG GTGATCACAA ACAGTAAGGT    6900
GAGCGAGCGC ACCTACATGG GTGCAGAATC TTGTGTGCTC ATCTATCCTA ATTCGGTAAT    6960
TCCTATCCAG CGCTAGTCTT GTGACCATGG GGCATGGGTT CGACTCTGTG ACAGGGCATC    7020
CAAGAGGCTG ATCACCCGGA AGAAGGGTAC TACCGTACTA TAAGGTCTGG AATCGTGGTG    7080
ATCTTGAAGA ATGCAACCAT CAACGATGGG TCTGTCATAT AGATCGGCTG CGTGTGCGTC    7140
TACAAAACAA GAACCTACAA TGGTATTGCA TCGATGGATC GTGTAACCTT GGTATGGTAA    7200
GAGCCGCTTG ACAGAAAGTC GAGCGTTCGG GCAAGATGCG TAGTCTGGCA TGCTGTTCCT    7260
TGACCATTTG TGCTGCTAGT ATGTACTGTT ATAAGCTGCC CTAGAAGTTG CAGCAAACCT    7320
TTTTATGAAC CTTTGTATTT CCATTACCTG CTTTGGATCA ACTATATCTG TCATCCTATA    7380
TATTACTAAA TTTTTACGTG TTTTTCTAAT TCGGTGCTGC TTTTGGGATC TGGCTTCGAT    7440
GACCGCTCGA CCCTGGGCCA TTGGTTCAGC TCTGTTCCTT AGAGCAACTC CAAGGAGTCC    7500
TAAATTTTGT ATTAGATACG AAGGACTTCA GCCGTGTATG TCGTCCTCAC CAAACGCTCT    7560
TTTTGCATAG TGCAGGGGTT GTAGACTTGT AGCCCTTGTT TAAAGAGGAA TTTGAATATC    7620
AAATTATAAG TATTAAATAT ATATTTAATT AGGTTAACAA ATTTGGCTCG TTTTTAGTCT    7680
TTATTTATGT AATTAGTTTT AAAAATAGAC CTATATTTCA ATACGAAATA TCATTAACAT    7740
CGATA                                                                7745
```

( 2 ) INFORMATION FOR SEQ ID NO:2:

( i ) SEQUENCE CHARACTERISTICS:
        ( A ) LENGTH: 518 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140
```

| | | | | | | | | | | | | | | |
|---|---|---|---|---|---|---|---|---|---|---|---|---|---|---|
| Asn 145 | Arg | His | Ile | His | Arg 150 | Thr | Tyr | Leu | Glu | Gly 155 | Gly | Ile | Asn | Phe | Ala 160 |
| Asp | Gly | Ser | Val | Gln 165 | Val | Leu | Ala | Ala | Thr 170 | Gln | Met | Pro | Glu | Glu 175 | Pro |
| Ala | Gly | Trp | Phe 180 | Gln | Gly | Thr | Ala | Asp 185 | Ser | Ile | Arg | Lys | Phe 190 | Ile | Trp |
| Val | Leu | Glu 195 | Asp | Tyr | Tyr | Ser | His 200 | Lys | Ser | Ile | Asp | Asn 205 | Ile | Val | Ile |
| Leu | Ser 210 | Gly | Asp | Gln | Leu | Tyr 215 | Arg | Met | Asn | Tyr | Met 220 | Glu | Leu | Val | Gln |
| Lys 225 | His | Val | Glu | Asp 230 | Asp | Ala | Asp | Ile | Thr 235 | Ile | Ser | Cys | Ala | Pro | Val 240 |
| Asp | Glu | Ser | Arg | Ala 245 | Ser | Lys | Asn | Gly | Leu 250 | Val | Lys | Ile | Asp | His 255 | Thr |
| Gly | Arg | Val | Leu 260 | Gln | Phe | Phe | Glu | Lys 265 | Pro | Lys | Gly | Ala | Asp 270 | Leu | Asn |
| Ser | Met | Arg 275 | Val | Glu | Thr | Asn | Phe 280 | Leu | Ser | Tyr | Ala | Ile 285 | Asp | Asp | Ala |
| Gln | Lys 290 | Tyr | Pro | Tyr | Leu | Ala 295 | Ser | Met | Gly | Ile | Tyr 300 | Val | Phe | Lys | Lys |
| Asp 305 | Ala | Leu | Leu | Asp | Leu 310 | Leu | Lys | Ser | Lys | Tyr 315 | Thr | Gln | Leu | His | Asp 320 |
| Phe | Gly | Ser | Glu | Ile 325 | Leu | Pro | Arg | Ala | Val 330 | Leu | Asp | His | Ser | Val 335 | Gln |
| Ala | Cys | Ile | Phe 340 | Thr | Gly | Tyr | Trp | Glu 345 | Asp | Val | Gly | Thr | Ile 350 | Lys | Ser |
| Phe | Phe | Asp 355 | Ala | Asn | Leu | Ala | Leu 360 | Thr | Glu | Gln | Pro | Ser 365 | Lys | Phe | Asp |
| Phe | Tyr 370 | Asp | Pro | Lys | Thr | Pro 375 | Phe | Phe | Thr | Ala | Pro 380 | Arg | Cys | Leu | Pro |
| Pro 385 | Thr | Gln | Leu | Asp | Lys 390 | Cys | Lys | Met | Lys | Tyr 395 | Ala | Phe | Ile | Ser | Asp 400 |
| Gly | Cys | Leu | Leu | Arg 405 | Glu | Cys | Asn | Ile | Glu 410 | His | Ser | Val | Ile | Gly 415 | Val |
| Cys | Ser | Arg | Val 420 | Ser | Ser | Gly | Cys | Glu 425 | Leu | Lys | Asp | Ser | Val 430 | Met | Met |
| Gly | Ala | Asp 435 | Ile | Tyr | Glu | Thr | Glu 440 | Glu | Glu | Ala | Ser | Lys 445 | Leu | Leu | Leu |
| Ala | Gly 450 | Lys | Val | Pro | Ile | Gly 455 | Ile | Gly | Arg | Asn | Thr 460 | Lys | Ile | Arg | Asn |
| Cys 465 | Ile | Ile | Asp | Met 470 | Asn | Ala | Arg | Ile | Gly 475 | Lys | Asn | Val | Val | Ile 480 |
| Asn | Ser | Lys | Gly | Ile 485 | Gln | Glu | Ala | Asp | His 490 | Pro | Glu | Glu | Gly 495 | Tyr | Tyr |
| Arg | Thr | Ile | Arg 500 | Ser | Gly | Ile | Val | Val 505 | Ile | Leu | Lys | Asn | Ala 510 | Thr | Ile |
| Asn | Glu | Cys 515 | Leu | Val | Ile | | | | | | | | | | |